(12) United States Patent
Kroll

(10) Patent No.: US 7,676,266 B1
(45) Date of Patent: Mar. 9, 2010

(54) MONITORING VENTRICULAR SYNCHRONY

(75) Inventor: Mark W. Kroll, Crystal Bay, MN (US)

(73) Assignee: Pacesetter, Inc., Sylmar, CA (US)

( * ) Notice: Subject to any disclaimer, the term of this patent is extended or adjusted under 35 U.S.C. 154(b) by 395 days.

(21) Appl. No.: 11/830,617

(22) Filed: Jul. 30, 2007

(51) Int. Cl.
*A61N 1/365* (2006.01)

(52) U.S. Cl. ............................. 607/18; 607/16; 607/17; 600/486

(58) Field of Classification Search ............... 607/9–26; 600/480–490, 510–530; 601/41; 126/637
See application file for complete search history.

(56) References Cited

U.S. PATENT DOCUMENTS

| | | | |
|---|---|---|---|
| 4,712,555 A | 12/1987 | Thornander et al. | |
| 4,788,980 A | 12/1988 | Mann et al. | |
| 4,940,052 A | 7/1990 | Mann et al. | |
| 4,944,298 A | 7/1990 | Sholder | |
| 5,305,745 A * | 4/1994 | Zacouto | 600/324 |
| 5,466,254 A | 11/1995 | Helland | |
| 5,476,483 A | 12/1995 | Bornzin et al. | |
| 6,314,323 B1 | 11/2001 | Ekwall | |
| 7,286,875 B1 * | 10/2007 | Park et al. | 607/18 |
| 2003/0204212 A1 | 10/2003 | Burnes et al. | |
| 2004/0172077 A1 | 9/2004 | Chinchoy | |
| 2005/0027322 A1 * | 2/2005 | Warkentin | 607/17 |
| 2005/0038481 A1 | 2/2005 | Chinchoy et al. | |
| 2005/0182447 A1 | 8/2005 | Schecter | |
| 2007/0055170 A1 * | 3/2007 | Lippert et al. | 600/547 |
| 2008/0269816 A1 * | 10/2008 | Prakash et al. | 607/9 |

FOREIGN PATENT DOCUMENTS

| WO | WO 2004/078254 A2 | 9/2004 |
|---|---|---|
| WO | WO 2005/018740 A1 | 3/2005 |

OTHER PUBLICATIONS

Notomi et al, "Assessment of Left Ventricular Torsional Deformation by Doppler Tissue Imaging: Validation Study With Tagged Magnetic Resonance Imaging," Circulation 2005;111;1141-1147.

* cited by examiner

*Primary Examiner*—Carl H Layno
*Assistant Examiner*—Paula J Stice

(57) ABSTRACT

An exemplary method includes providing a maximum right ventricular systolic pressure value and corresponding time during a cardiac cycle, providing a left ventricular displacement value for the corresponding time, determining a product of the maximum right ventricular systolic pressure value and the magnitude of the left ventricular displacement value and assessing ventricular synchrony for the cardiac cycle based at least in part on the product. Such a method may include adjusting one or more cardiac pacing parameters based at least in part on the product. Other exemplary methods, devices, systems, etc., are also disclosed.

16 Claims, 11 Drawing Sheets

Exemplary Electrode Arrangement wrt
Ventricular Mechanics
600

MONITORING VENTRICULAR SYNCHRONY

TECHNICAL FIELD

Subject matter presented herein generally relates to techniques to assess ventricular synchrony or asynchrony. Such techniques may aid diagnosis of cardiac condition and selection of or adjustment to cardiac pacing therapy.

BACKGROUND

Clinical studies related to cardiac pacing have shown that an optimal atrio-ventricular delay (e.g., AV delay) and/or an optimal interventricular delay (e.g., VV delay) can improve cardiac performance. While various techniques can assess ventricular synchrony to help determine such delays, these techniques typically require visits to a clinic where echocardiography or other imaging equipment is available. Thus, a need exists for techniques that can assess ventricular synchrony on a more regular basis, optionally without disturbing a patient's schedule. Various exemplary techniques discussed herein aim to meet this need and/or other needs. Further, such techniques may allow for diagnosing patient condition and/or selection or adjusting pacing therapy.

SUMMARY

An exemplary method includes providing a maximum right ventricular systolic pressure value and corresponding time during a cardiac cycle, providing a left ventricular displacement value for the corresponding time, determining a product of the maximum right ventricular systolic pressure value and the magnitude of the left ventricular displacement value and assessing ventricular synchrony for the cardiac cycle based at least in part on the product. Such a method may include adjusting one or more cardiac pacing parameters based at least in part on the product. Other exemplary methods, devices, systems, etc., are also disclosed. In general, the various methods, devices, systems, etc., described herein, and equivalents thereof, are suitable for use in a variety of pacing therapies and/or other cardiac related therapies.

BRIEF DESCRIPTION OF THE DRAWINGS

Features and advantages of the described implementations can be more readily understood by reference to the following description taken in conjunction with the accompanying drawings.

DETAILED DESCRIPTION

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims.

OVERVIEW

Exemplary methods, devices, systems, etc., aim to assess ventricular synchrony or lack thereof (i.e., asynchrony or dyssynchrony). Various exemplary methods include measuring right ventricular pressure and left ventricular motion impedance over one or more cardiac cycles and optionally over one or more respiratory cycles. Right ventricular pressure provides information related to contraction of the right ventricle while left ventricular motion impedance provides information as to contraction of the left ventricle. As described herein, a negative correlation product of right ventricular pressure and left ventricular motion impedance may be used as an indicator of ventricular synchrony or asynchrony. Such an indicator may be used to call for an adjustment to a therapy, to call for selection of a therapy or in determining one or more pacing parameters. As impedance measurements may be available from multiple left ventricular sites, techniques for optimizing stimulation site selection are also presented.

The following description begins with a discussion of exemplary implantable devices and associated components followed by a discussion of cardiac mechanics (e.g., pressures, velocities, etc.). A discussion of exemplary electrode arrangements for impedance measurements follows along with a discussion of various exemplary methods, devices, systems, etc.

Exemplary Stimulation Device

The techniques described below are intended to be implemented in connection with any stimulation device that is configured or configurable to stimulate nerves and/or stimulate and/or shock a patient's heart.

Figure 1:
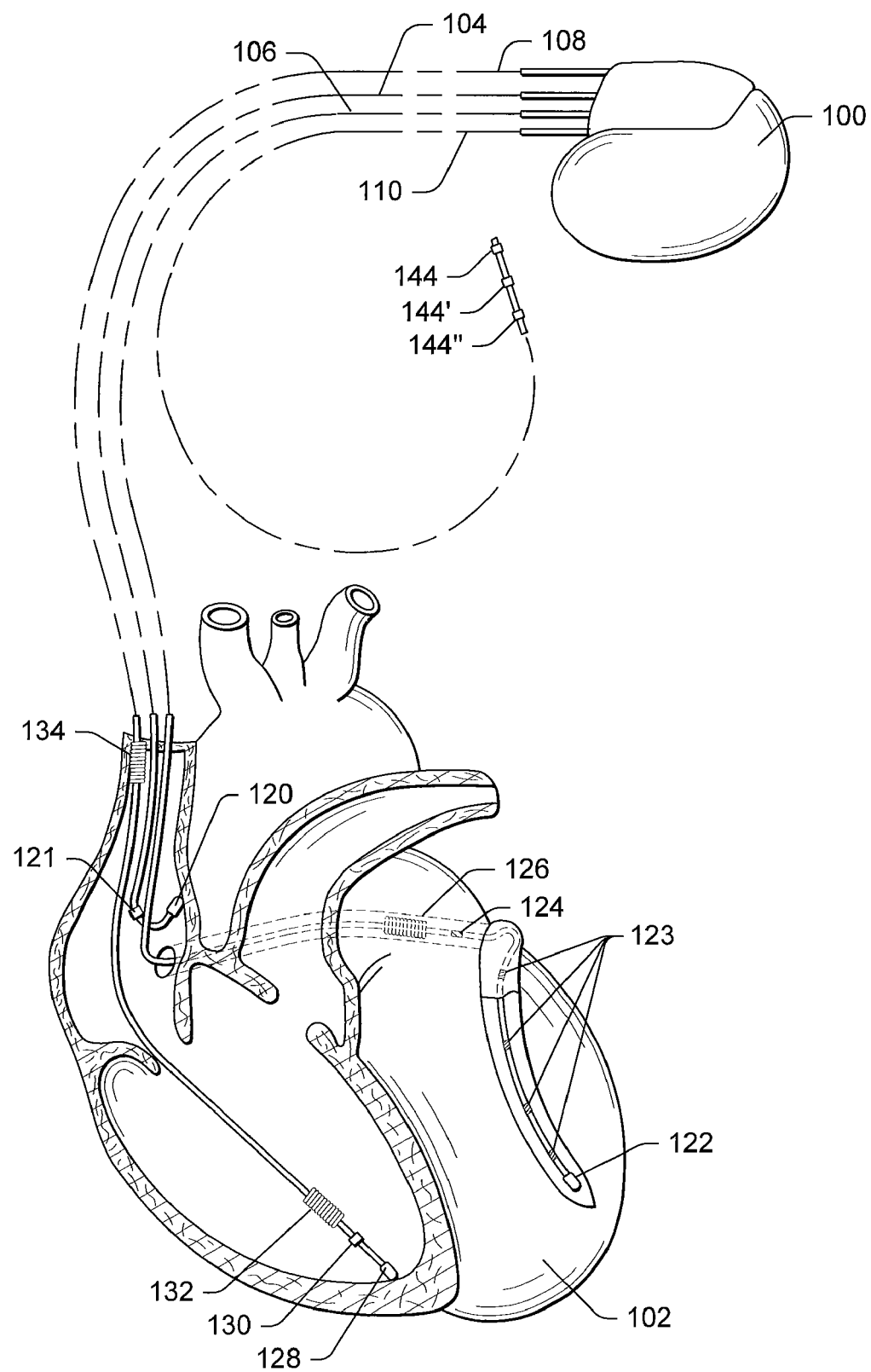
FIG. 1 is a simplified diagram illustrating an exemplary implantable stimulation device in electrical communication with at least three leads implanted into a patient's heart and at least one other lead for delivering stimulation and/or shock therapy and/or sensing information. Other devices with fewer leads may also be suitable in some circumstances.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of non-myocardial tissue (e.g., nerves, other muscle, etc.). In addition, the device 100 includes a fourth lead 110 having, in this implementation, three electrodes 144, 144', 144" suitable for any of a variety of tissue stimulation and/or physiologic sensing. For example, this lead may be positioned in and/or near a patient's heart or near an autonomic nerve within a patient's body and remote from the heart. Of course, such a lead may be positioned epicardially or at some other location to stimulate other tissue. The lead 110 may include one or more sensors (e.g., pressure, pH, blood gas, etc.).

The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation with electrodes on one or both branches.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or a tributary vein of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

In the example of FIG. 1, the coronary sinus lead 106 includes a series of electrodes 123. In particular, a series of four electrodes are shown positioned in an anterior vein of the heart 102. Other coronary sinus leads may include a different number of electrodes than the lead 106. As described herein, an exemplary method may select one or more electrodes (e.g., from electrodes 123 of the lead 106) and determine characteristics associated with conduction in the heart to aid in ventricular pacing therapy, to determine impedance as related to motion of the left ventricle, to deliver energy to the heart, etc.

An exemplary coronary sinus lead 106 may be used to receive ventricular cardiac signals (and optionally atrial signals) and/or to deliver left ventricular pacing therapy using, for example, at least one of the electrodes 123 and/or the tip electrode 122. The lead 106 optionally allows for left atrial pacing therapy, for example, using at least the left atrial ring electrode 124. The lead 106 optionally allows for shocking therapy, for example, using at least the left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference.

The coronary sinus lead 106 further optionally includes electrodes for stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve, such an electrode may be positioned on the lead or a bifurcation or leg of the lead.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include an electrode capable of stimulating an autonomic nerve, such an electrode may be positioned on the lead or a bifurcation or leg of the lead.

Figure 2:
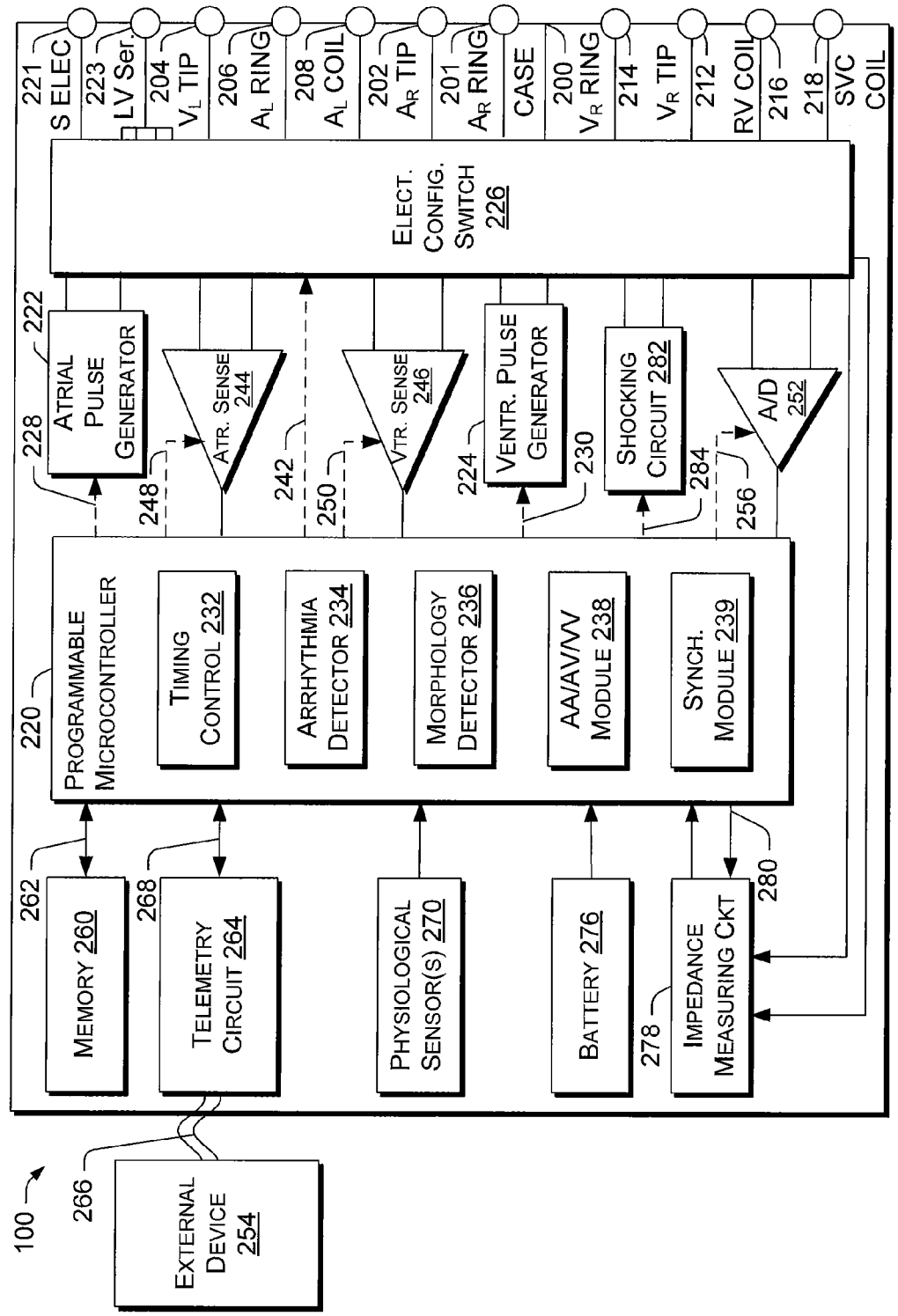
FIG. 2 is a functional block diagram of an exemplary implantable stimulation device illustrating basic elements that are configured to provide cardioversion, defibrillation, pacing stimulation and/or other tissue and/or nerve stimulation. The implantable stimulation device is further configured to sense information and to optionally administer stimulation pulses responsive to or based on such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. While a particular multi-chamber device is shown, it is to be appreciated and understood that this is done for illustration purposes only. For example, various methods may be implemented on a pacing device suited for single ventricular stimulation and not bi-ventricular stimulation. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, and/or autonomic nerve stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

Other terminals may be included, for example, to accommodate other electrodes of other leads. Further, where appropriate, epicardial or other types of leads or electrodes may be connected to the device 100 or to a device in communication with the device 100 to provide for coordinated pacing therapy (e.g., CRT or other pacing therapy).

To achieve right atrial sensing and/or pacing, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing and/or shocking, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively.

A terminal (LV Ser.) 223 allows for connection of a series of left ventricular electrodes. For example, the series of four electrodes 123 of the lead 106 may connect to the device 100 via the terminal 223. The terminal 223 and an electrode configuration switch 226 allow for selection of one or more of the series of electrodes and hence electrode configuration. In the example of FIG. 2, the terminal 223 includes four branches to the switch 226 where each branch corresponds to one of the four electrodes 123. An implantable device may include other terminals and/or terminal arrangements. For example, the terminal S ELEC 221 may be used for connecting to a lead configured for stimulation and/or sensing of nerves or other tissue.

To support right chamber sensing, pacing and/or shocking, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively.

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. The switch 226 may also be used to select one or more electrodes associated with the lead 110. It is understood that in order to provide stimulation therapy in each of the four chambers of the heart (or to other tissue), the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit stimulation pulses.

Microcontroller 220 further includes timing control circuitry 232 to control the timing of the stimulation pulses (e.g., pacing rate, atrio-ventricular (e.g., AV) delay, atrial interconduction (AA) delay, or ventricular interconduction (VV) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module, the latter two are not shown in FIG. 2. The various components can be utilized by the stimulation device 100 for determining desirable times to administer therapies, for example, including therapies to reduce the effects of orthostatic hypotension. The aforementioned components may be implemented in hardware as part of the microcontroller 220, or as software/firmware instructions programmed into the device and executed on the microcontroller 220 during certain modes of operation.

Microcontroller 220 further includes an AA delay, AV delay and/or VV delay module 238 for performing a variety of tasks related to AA delay, AV delay and/or VV delay. This component can be utilized by the stimulation device 100 for determining desirable times to administer various therapies, including, but not limited to, ventricular stimulation therapy, biventricular stimulation therapy, resynchronization therapy, atrial stimulation therapy, etc. The AA/AV/VV module 238 may be implemented in hardware as part of the microcontroller 220, or as software/firmware instructions programmed into the device and executed on the microcontroller 220 during certain modes of operation. Of course, such a module may be limited to one or more of the particular functions of AA delay, AV delay and/or VV delay. Such a module may include other capabilities related to other functions that may be germane to the delays.

The microcontroller 220 includes a synchronization module 239 for performing a variety of tasks related to ventricular synchrony or asynchrony. This component can be utilized by the stimulation device 100 for implementing various exemplary methods described herein. The module 239 may operate in conjunction with one or more other modules. For example, the module 239 may operate in conjunction with the AA/AV/VV module 238 for administration of various therapies, including, but not limited to, ventricular stimulation therapy, biventricular stimulation therapy, resynchronization therapy, atrial stimulation therapy, etc. The synchronization module 239 may be implemented in hardware as part of the microcontroller 220, or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers.

Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. In some instances, detection or detecting includes sensing and in some instances sensing of a particular signal alone is sufficient for detection (e.g., presence/absence, etc.).

The timing intervals between sensed events (e.g., P-waves, R-waves, and depolarization signals associated with fibrillation) are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals or other signals may be applied to inputs of an analog-to-digital (A/D) data acquisition system 252. The data acquisition system 252 is typically configured to acquire intracardiac electrogram (IEGM) signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the lead 110 through the switch 226 to sample cardiac or other signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include one or more physiologic sensors 270. For example, the device 100 can include a sensor commonly referred to as a "rate-responsive" sensor because it is typically used to adjust pacing stimulation rate according to the exercise state of the patient. The device 100 can include a physiological sensor to detect (i) changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), (ii) changes in the physiological condition of the heart, or (iii) diurnal changes in activity (e.g., detecting sleep and wake states). In response to a change, the microcontroller 220 can respond by adjusting one or more pacing parameters (such as rate, AA delay, AV delay, VV delay, etc.).

As described below, various exemplary methods may use information acquired through use of a right ventricular pressure sensor where the physiological sensor 270 provides such information to the microcontroller 220. The synchronization module 239 may use the pressure information to assess ventricular synchrony or asynchrony, for example, in conjunction with impedance or other motion information associated with the left ventricle.

While the one or more physiologic sensors 270 are shown as being included within the stimulation device 100, it is to be understood that a physiologic sensor may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, hemodynamics, pressure, and so forth. Another sensor that may be used is one that detects activity variance, wherein an activity sensor is monitored diurnally to detect the low variance in the measurement corresponding to the sleep state.

For a complete description of the activity variance sensor, the reader is directed to U.S. Pat. No. 5,476,483 (Bornzin et al.), issued Dec. 19, 1995, which patent is hereby incorporated by reference.

The physiological sensors 270 optionally include sensors for detecting movement and minute ventilation in the patient. For example, the device 100 may include a position sensor and/or a minute ventilation (MV) sensor to sense minute ventilation, which is defined as the total volume of air that moves in and out of a patient's lungs in a minute. Signals generated by the position sensor and MV sensor can be passed to the microcontroller 220 for analysis in determining whether to adjust the pacing rate, etc. The microcontroller 220 can monitor these signals for indications of the patient's position and activity status, such as whether the patient is climbing upstairs or descending downstairs or whether the patient is sitting up after lying down.

With respect to motion or movement sensors, a lead may include an accelerometer that can output a signal to the data acquisition system 252 or other circuitry of the device 100. While various examples use impedance as a measure of left ventricular motion, an accelerometer may be positioned on or in the left ventricle to acquire information about left ventricular motion. Accelerometers typically include two or three sensors aligned along orthogonal axes. For example, a commercially available micro-electromechanical system (MEMS) marketed as the ADXL202 by Analog Devices, Inc. (Norwood, Mass.) has a mass of about 5 grams and a 14 lead CERPAK (approx. 10 mm by 10 mm by 5 mm or a volume of approx. 500 mm$^3$). The ADXL202 MEMS is a dual-axis accelerometer on a single monolithic integrated circuit and includes polysilicon springs that provide a resistance against acceleration forces. The term MEMS has been defined generally as a system or device having micro-circuitry on a tiny silicon chip into which some mechanical device such as a mirror or a sensor has been manufactured. The aforementioned ADXL202 MEMS includes micro-circuitry and a mechanical oscillator.

Another commercially available MEMS accelerometer is the ADXL330 by Analog Devices, Inc., which is a small, thin, low power, complete three axis accelerometer with signal conditioned voltage outputs, all on a single monolithic IC (about 4 mm by 4 mm by 1.45 mm). The ADXL330 product measures acceleration with a minimum full-scale range of ±3 g. It can measure the static acceleration of gravity in tilt-sensing applications, as well as dynamic acceleration resulting from motion, shock, or vibration. Bandwidths can be selected to suit the application, with a range of 0.5 Hz to 1,600 Hz for X and Y axes, and a range of 0.5 Hz to 550 Hz for the Z axis.

The stimulation device 100 additionally includes a battery 276 as a power source that provides operating power to all of the circuits shown in FIG. 2. The battery 276 is generally capable of operating at low current drains for long periods of time (e.g., preferably less than 10 μA) and is capable of providing high-current pulses (for capacitor charging) when the patient requires a shock pulse (e.g., preferably, in excess of 2 A, at voltages above 2 V, for periods of 10 seconds or more). The battery 276 typically has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264. A magnet may signal the device 100 to acquire and store IEGMs.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used. As described herein, various exemplary methods may use the circuit 278 to acquire impedance information related to left ventricular motion. In turn, such information may be used by the synchronization module 239 to assess ventricular synchrony or asynchrony.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to approximately 0.5 J), moderate (e.g., approximately 0.5 J to approximately 10 J), or high energy (e.g., approximately 11 J to approximately 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode). Other exemplary devices may include one or more other coil electrodes or suitable shock electrodes (e.g., a LV coil, etc.).

Cardioversion level shocks are generally considered to be of low to moderate energy level (where possible, so as to minimize pain felt by the patient), and/or synchronized with an R-wave and/or pertaining to the treatment of tachycardia. Defibrillation shocks are generally of moderate to high energy level (i.e., corresponding to thresholds in the range of approximately 5 J to approximately 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Figure 3:
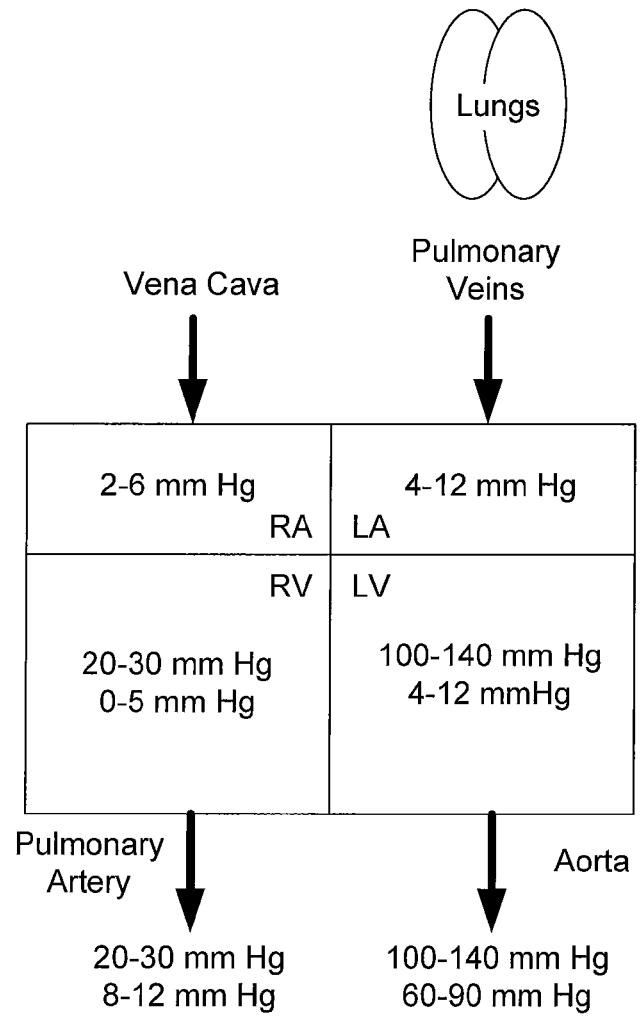
FIG. 3 is a schematic diagram of blood flow for the heart and lungs that also lists various blood pressures.

For a better appreciation of cardiac pressures, FIG. 3 shows a diagram 300 with various approximate, normal cardiac pressures values. Blood enters the right atrium (RA) from the vena cava and the coronary sinus ostium. RA blood pressures are typically in a range from about 2 mm Hg to about 6 mm Hg. The RA fills the right ventricle (RV) where pressure varies significantly between diastolic and systolic phases of the cardiac cycle. For example, the diastolic pressure may fall in a range from about 0 mm Hg to about 5 mm Hg while the systolic pressure is greater, normally about 20 mm Hg to about 30 mm Hg; noting for diseased states, the right ventricular systolic pressure may exceed 50 mm Hg. Myocardial contraction forces blood from the RV to the lungs via the pulmonary artery, where systolic phase pressures are in a range from about 20 mm Hg to about 30 mm Hg. Diastolic phase pressures in the pulmonary artery are typically in a range from about 8 mm Hg to about 12 mm Hg.

Blood returns from the lungs to the heart via the pulmonary veins at the left atrium (LA), where pressures typically range from about 4 mm Hg to about 12 mm Hg. Blood from the LA enters the left ventricle (LV), which generates the greatest cardiac pressures. Normal systolic phase pressures range from about 100 mm Hg to about 140 mm Hg. Normal diastolic phase pressures range from about 4 mm Hg to about 12 mm Hg.

The LV ejects about 70 ml of blood per contraction into the aorta, typically referred to as LV stroke volume or simply stroke volume. The LV experiences normal systolic phase pressures that vary from about 100 mm Hg to about 140 mm Hg and normal diastolic phase pressures that vary from about 60 mm Hg to about 90 mm Hg. In some instances, these so-called normal ranges are subdivided (e.g., normal-low, normal-high, etc.). Common blood pressure tests monitor pressures closely associated with aortic flow. Further, pulse measurements reflect LV dynamics and aortic flow, as well as valve mechanics.

Cardiac pressures, including pressures of associated vessels, are often analyzed on the basis of systolic and diastolic phases; however, as explained herein, respiration affects cardiac pressures. In most instances, respiration occurs at a lesser frequency than myocardial contraction, i.e., respiration rate is typically less than heart rate. Consequently, several cardiac cycles occur per respiratory cycle. The respiratory cycle includes an expiratory phase and an inspiratory phase. While these respiratory phases alter heart rate to some degree (e.g., respiratory sinus arrhythmia), they also alter cardiac pressures and stroke volume. Further, some cardiac conditions alter the relationship between respiration and cardiac pressures and stroke volume.

Figure 4:
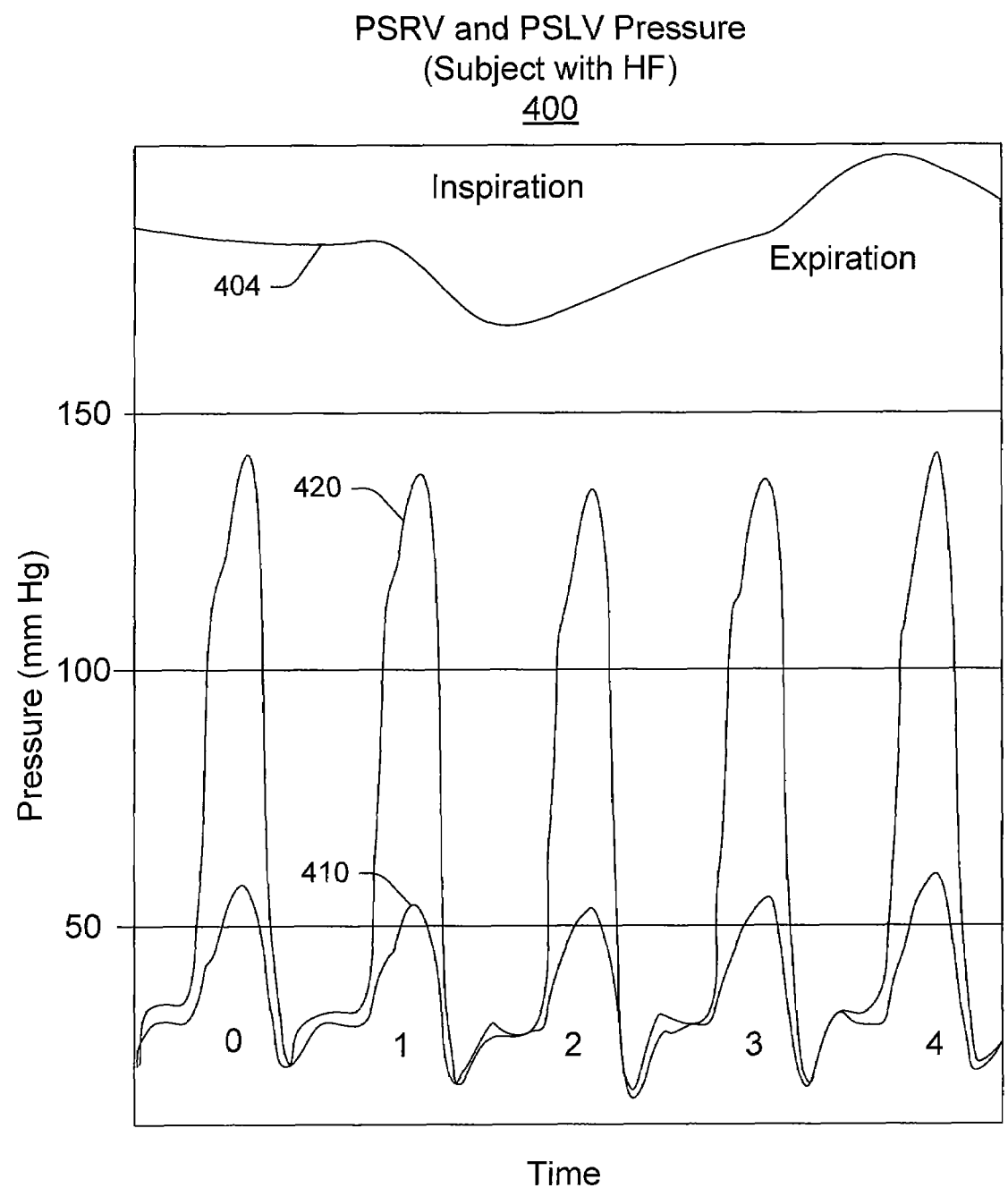
FIG. 4 is a series of plots that demonstrate a relationship between respiration and left and right ventricular pressure.

FIG. 4 shows a plot 400 of right ventricular systolic and diastolic pressures 410 and left ventricular systolic and diastolic pressures 420 versus time for about one respiration cycle, which, for this example, corresponds to about five cardiac cycles (labeled 0-4). Respiration is indicated as a decrease in intrathoracic pressure for inspiration and a return to a baseline intrathoracic pressure for expiration, noting that forced expiration can cause intrathoracic pressure to rise considerably above the baseline. These data were reported in a study by Hurrell et al., "Value of Dynamic Respiratory Changes in Left and Right Ventricular Pressures for the Diagnosis of Constrictive Pericarditis", *Circulation*, 1996; 93: 2007-2013, and correspond to a group of patients (21 patients) having some degree of heart failure other than constrictive pericarditis (restrictive cardiomyopathy in 7, severe tricuspid regurgitation in 4, dilated cardiomyopathy in 3, ischemic cardiomyopathy in 4, aortic stenosis in 1, atrial septal defect in 1, and mitral prosthesis dysfunction in 1). Consequently, the right ventricular systolic pressure is elevated.

The systolic pressures labeled "1" correspond to the first cardiac cycle after the commencement of the inspiratory phase while the systolic pressures labeled "4" correspond to the first cardiac cycle after the commencement of the expiratory phase. For each cardiac cycle, the peak systolic right ventricular pressure (PSRV) and the peak systolic left ventricular pressure (PSLV) occur at about the same time, which may indicate some degree of ventricular synchrony. Further, the data indicate that peak systolic pressures decrease with inspiration and rise with expiration. In particular, the rise and fall in PSRV and PSLV occurs substantially in unison on a beat-by-beat basis or concordantly. Thus, the PSRV and PSLV decrease during peak inspiration due a negative intrathoracic pressure relative to ambient pressure.

Figure 5:
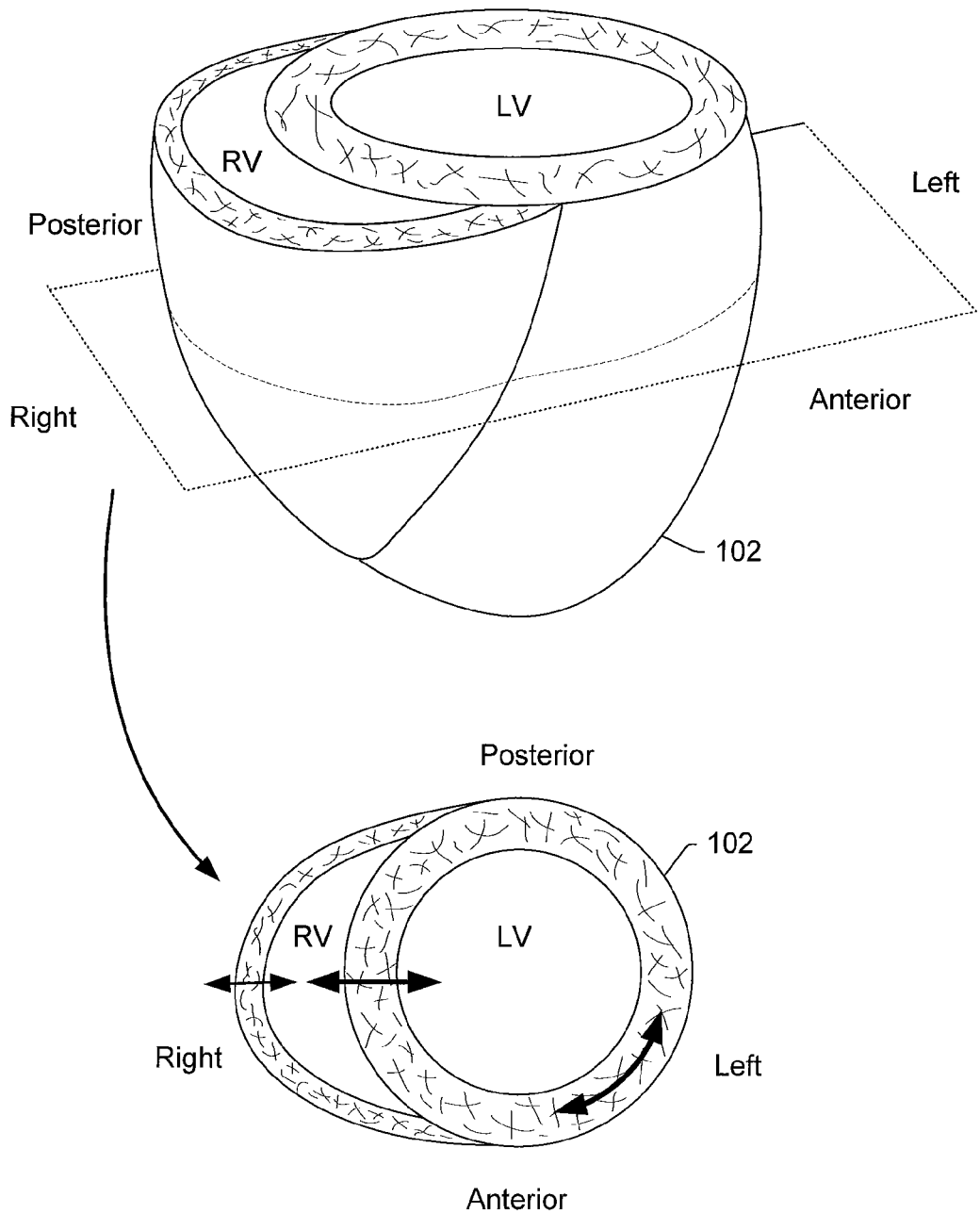
FIG. 5 is an approximate anatomical diagram of a heart for purposes of discussing ventricular mechanics.

FIG. 5 shows a perspective view and a cross-sectional view of the heart 102. In cross-section, the right ventricle has a crescent shape while the left ventricle has a somewhat circular shape. The right ventricle may be considered as a flattened tube wrapped around the left ventricle with separate inlet and outlet orifices with contraction pattern simulating peristalsis suitable for pumping blood against low resistance (e.g., to the lungs via the pulmonary artery). The left ventricle has a helical orientation of fibers that causes torsional deformation during contraction. Functional interaction between right and left ventricles occurs due to serial flow arrangement and the helical ventricular myocardial band of Torrent-Guasp. Further, changes in size and function of either ventricle may influence the performance of the other ventricle.

As shown in FIG. 5, the left ventricular wall moves in a helical manner, which causes movement of the septal wall, shared by the right and left ventricles. While the right ventricle also moves in a somewhat helical manner, during systole, right ventricular volume decreases due to motion of the right ventricular free wall toward the septal wall, motion of the base of the heart toward the apex and bulging of the septal wall into the right ventricular cavity.

Figure 6:
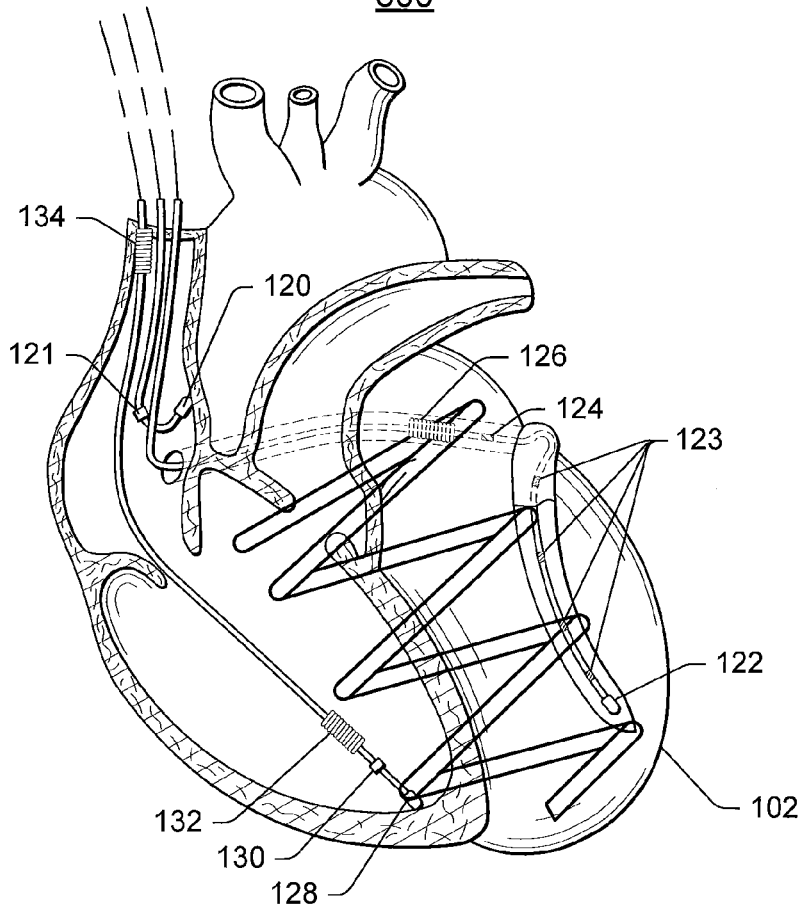
FIG. 6 is an approximate anatomical diagram of a heart together with various electrodes that may be used to measure impedance associated with left ventricular mechanics.
Figure 6:
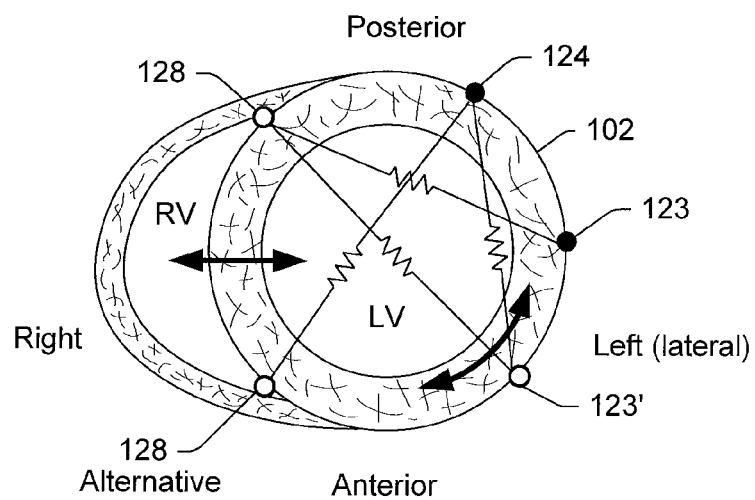

FIG. 6 shows an exemplary arrangement of electrodes 600, with reference to FIG. 1 and FIG. 5. FIG. 6 shows the view of the heart 102 from FIG. 1 with a helical coil aligned along the long axis of the left ventricle (e.g., from apex to base representing fiber orientation) and the cross-sectional view of the heart 102 from FIG. 5. The helical coil is solely to illustrate an approximate mechanism for contraction of the left ventricle. The cross-sectional view of the heart 102 includes approximate, possible positions for the electrodes 123, 124 and 128 along with some impedance paths. Hence, using the arrangement of electrodes 600, an implantable device may make one or more impedance measurements where impedance varies with respect to motion of the myocardium. In particular, an electrode configuration may include an electrode positioned in the right ventricle proximate or at the septal wall and an electrode positioned on the left ventricular lateral or "free wall", the posterior wall or the anterior wall. Using such arrangements, impedance measurements will vary with respect to motion of the left ventricle. As described herein, more than one impedance path may be used. Further, a can electrode may be used for measuring impedance.

Figure 7:
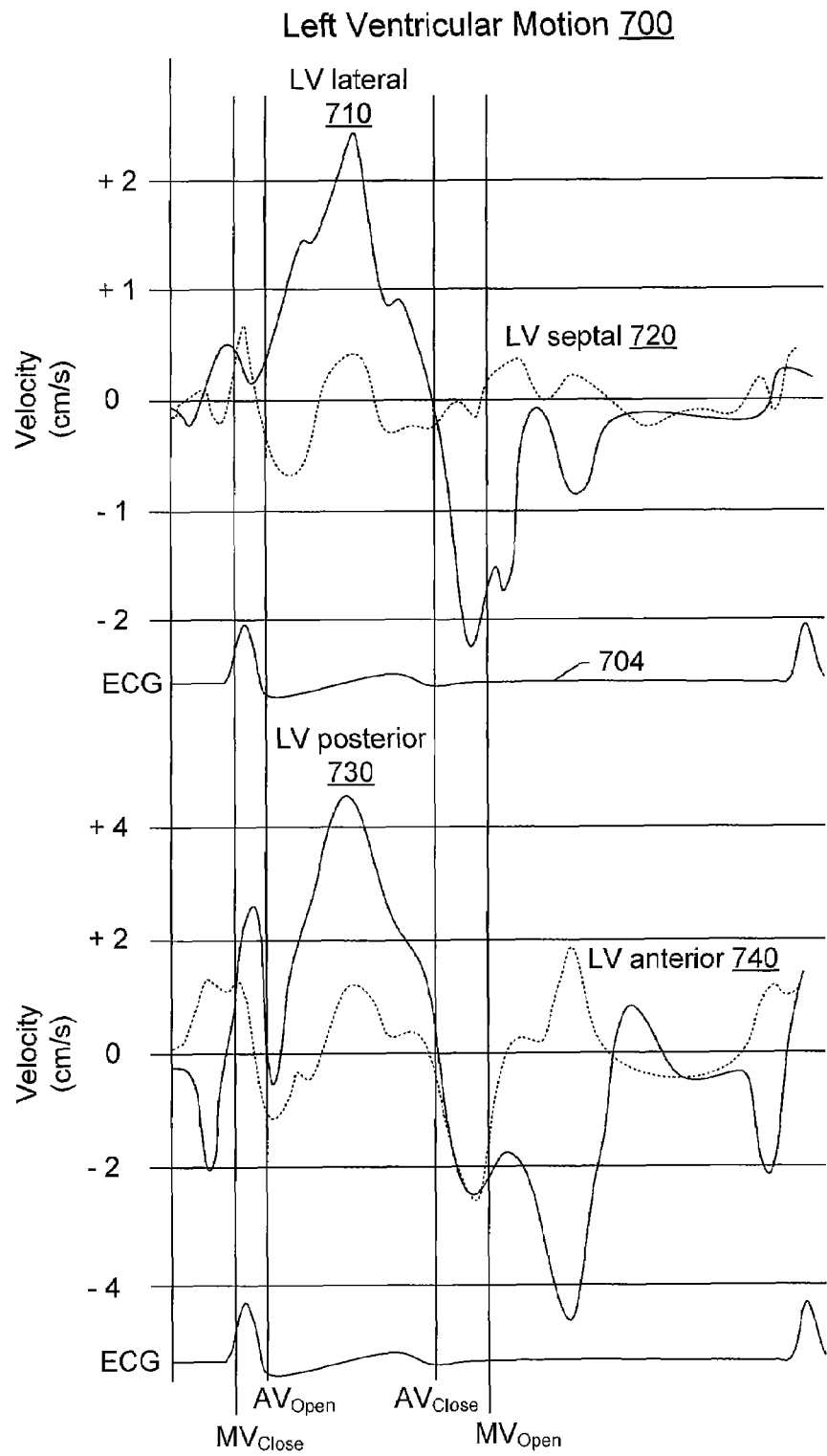
FIG. 7 is a series of velocity plots for various left ventricular walls over a cardiac cycle.

FIG. 7 shows a series of plots 700 of velocity versus time from a study by Notomi et al. ("Assessment of Left Ventricular Torsional Deformation by Doppler Tissue Imaging: Validation Study With Tagged Magnetic Resonance Imaging", *Circulation* 2005; 111; 1141-1147). The plots 700 also include an ECG 704. As indicated by the plots 700, the left ventricular posterior wall achieves the highest velocity (plot 730, e.g., about +/−4 cm/s) followed by the left ventricular lateral wall (plot 710, e.g., about +/−2 cm/s) whereas the septal wall has the smallest velocity (plot 720, e.g., less than about 0.5 cm/s). Consequently, an electrode arrangement that uses an electrode at or proximate to the septal wall and another electrode at the later or posterior wall can measure impedance where the impedance varies with respect to myocardial velocity.

Figure 8:
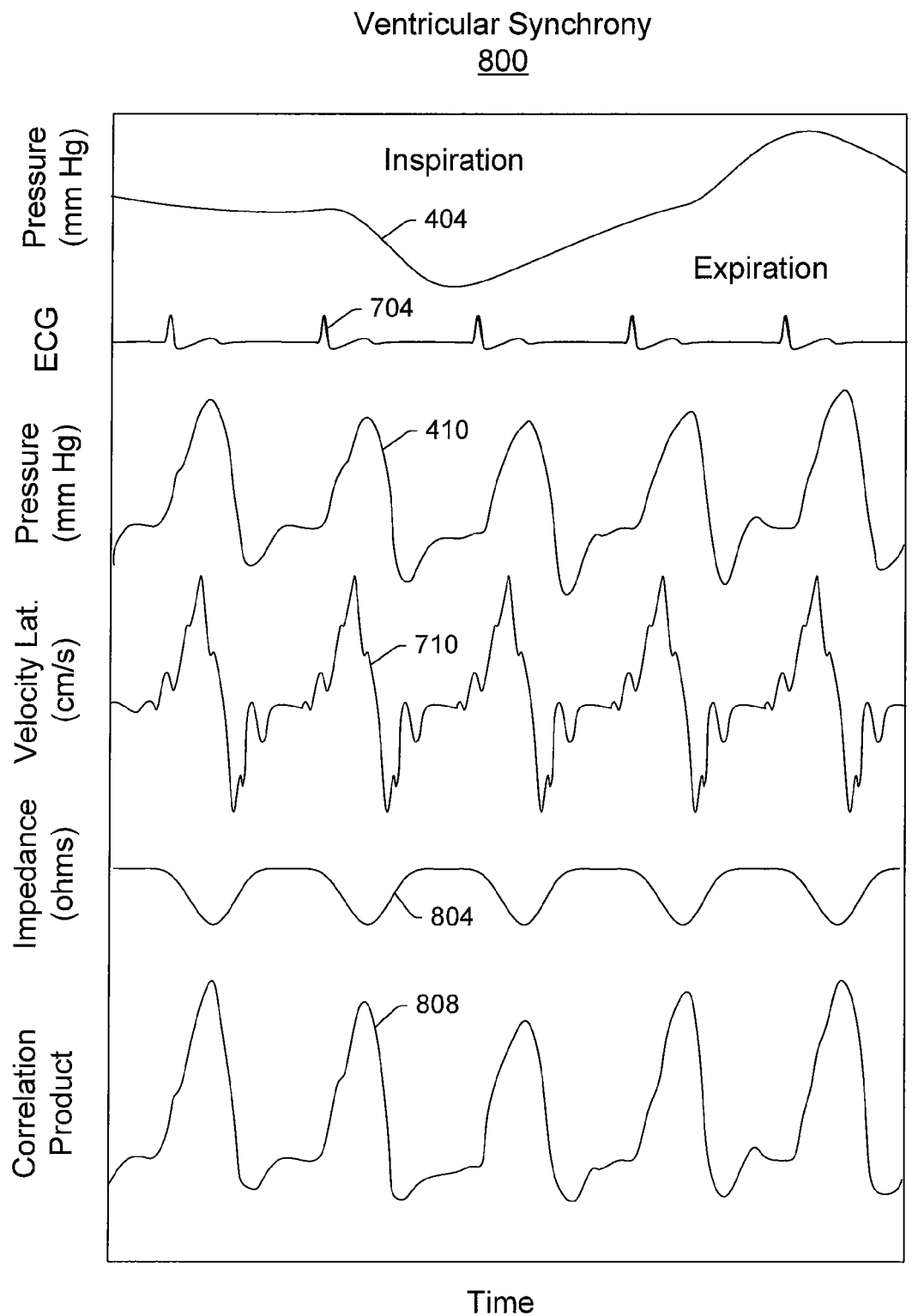
FIG. 8 is a series of plots for a patient with ventricular synchrony according to an exemplary method that calculates a correlation product based on right ventricular pressure and left ventricular motion impedance.

FIG. 8 shows a series of plots 800 that correspond to an exemplary method for a patient with ventricular synchrony. The plots 800 include data such as the data of the plots 404, 410 of FIG. 4 and the plots 704, 710 of FIG. 7. The plots 800 further include a plot of impedance versus time 804 and a negative correlation product of right ventricular pressure and impedance versus time 808. The negative correlation product of the plot 808 is the product of the right ventricular pressure (e.g., $P_{RV}$) and the magnitude of the impedance (e.g., Z) for various points in time (e.g., according to a sampling interval, etc.). Thus, for a time $t_1$, a negative correlation product plot would show $P_{RV}(t_1)*|Z(t_1)|$. While other equations may be used for pressure and impedance to assess ventricular synchrony or asynchrony, the negative correlation product provides an expeditious and relatively straightforward approach.

The plots 800 cover five cardiac cycles over about one respiratory cycle. As the negative correlation product 808 depends on the right ventricular pressure, the negative correlation product decreases with inspiration. In general, where ventricular synchrony exists, the peak systolic right ventricular pressure 410 and minimum impedance 804 occur at about the same time. Consequently, the negative correlation product has a maximum for ventricular synchrony according to the exemplary method.

Figure 9:
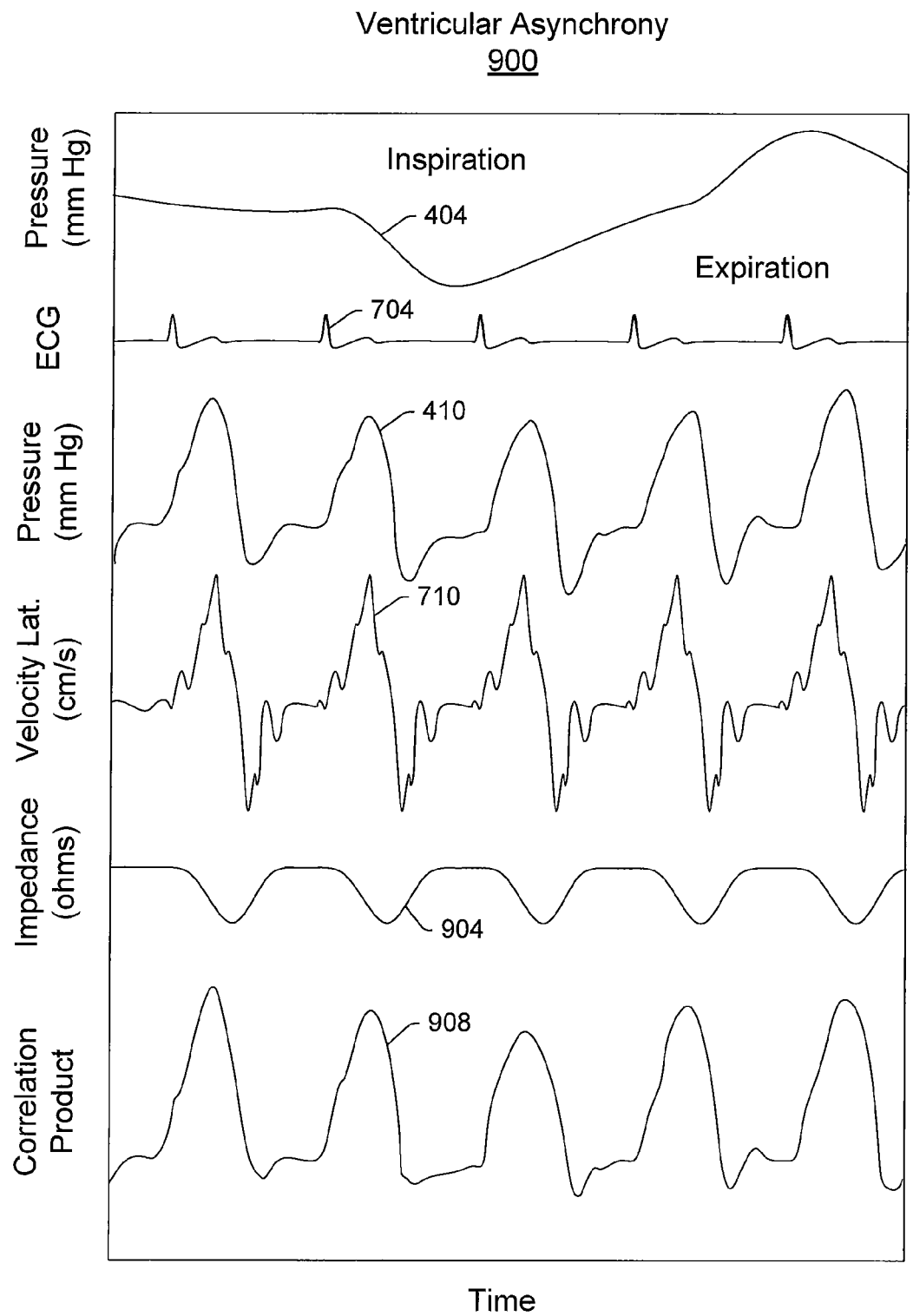
FIG. 9 is a series of plots for a patient with ventricular asynchrony according to an exemplary method that calculates a correlation product based on right ventricular pressure and left ventricular motion impedance.

FIG. 9 shows a series of plots 900 that correspond to the exemplary method of FIG. 8 for a patient with some degree of ventricular asynchrony. In this example, the left ventricle contracts after the right ventricle and thus the velocity increase and decrease of the left ventricular lateral wall 710 is delayed. In other words, movement of the left ventricular myocardium is shifted with respect to the peak in the right ventricular systolic pressure (PSRV). As described herein, the impedance measurement 904 depends primarily on motion of the left ventricle. Consequently, because the peak systolic right ventricular pressure 410 and minimum impedance 904 do not occur at the same time, the maximum value of the negative correlation product 908 is less than that for ventricular synchrony.

Figure 10:
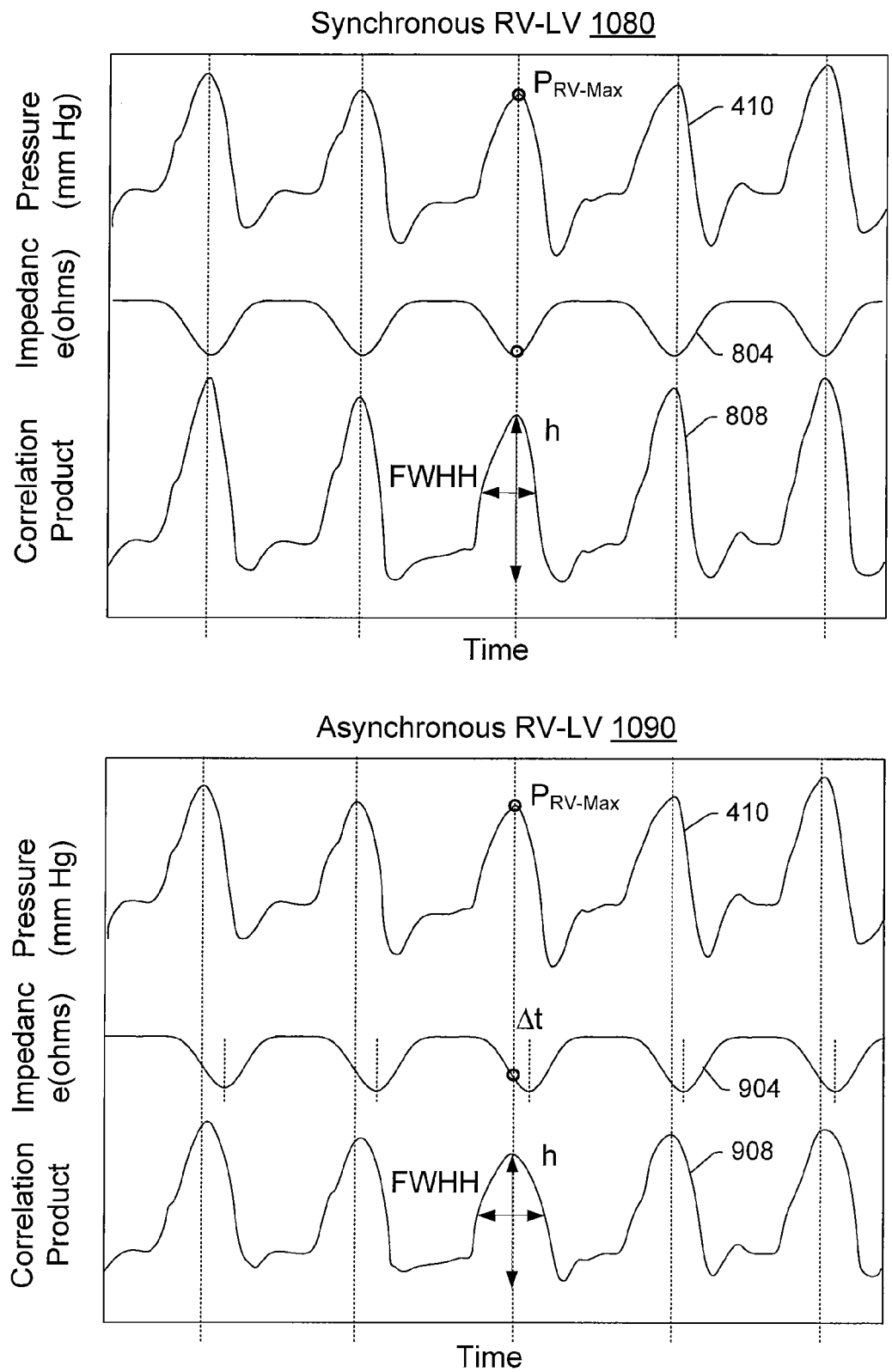
FIG. 10 is a series of plots comparing a correlation product for a patient with ventricular synchrony to a correlation product for a patient with ventricular asynchrony.

FIG. 10 shows a series of plots 1080 for ventricular synchrony and a series of plots 1090 for ventricular asynchrony. The series of plots 1080 includes the plots 410, 804 and 808 of FIG. 8 while the series of plots 1090 includes the plots 410, 904 and 908 of FIG. 9. A comparison of the plot 808 to the plot 908 reveals a decrease in height "h" and an increase in full width at half height "FWHH" with an increase in ventricular asynchrony. Also, for the plots 1080, the maximum right ventricular pressure for the third cardiac cycle occurs at about the same time as the minimum impedance. However, for the plots 1090, the maximum right ventricular pressure for the third cardiac cycle and the minimum impedance occur at different times, as indicated by a time delay $\Delta t$, which may be the time difference between the PSRV and the minimum impedance for a particular cardiac cycle. As PSRV may be expected to vary over a respiratory cycle, an exemplary method may average the negative correlation product height "h" and/or the width (e.g., FWHH). Other techniques may be used to account for variations in PSRV with respect to respiration.

An exemplary method includes providing a maximum right ventricular systolic pressure value and corresponding time during a cardiac cycle, providing a left ventricular displacement value for the corresponding time, determining a product of the maximum right ventricular systolic pressure value and the magnitude of the left ventricular displacement value and assessing ventricular synchrony for the cardiac cycle based at least in part on the product. As indicated by the plots 1080, 1090, the product corresponds to the height "h" of the plot 808 and 908. As already mentioned, this value may be used to assess ventricular synchrony or asynchrony. This particular method mentions left ventricular displacement value. Such a value may be an impedance value, based on an impedance value or other value that corresponds to displacement of part of the left ventricle during contraction. For example, the displacement value may correspond to a difference between displacement of the lateral wall with respect to the septal wall, optionally measured using an electrode in the right ventricle at the septal wall and another electrode in a vein that courses the lateral wall of the left ventricle.

An exemplary method includes acquiring right ventricular pressure during a cardiac cycle, acquiring left ventricular impedance during the cardiac cycle, determining a product of the right ventricular pressure and the magnitude of the left ventricular impedance and assessing ventricular synchrony for the cardiac cycle based at least in part on the product (see, e.g., the plots 808, 908).

An exemplary method includes acquiring right ventricular pressure over at least one respiratory cycle, acquiring left ventricular impedance over at least one respiratory cycle, determining a product of the right ventricular pressure and the magnitude of the left ventricular impedance and assessing ventricular synchrony for cardiac cycles occurring during the at least one respiratory cycle based at least in part on the product. Such a method may include averaging the maximum right ventricular pressure values for each cardiac cycle that occurs during the at least one respiratory cycle and averaging the left ventricular impedance values that correspond to each of the maximum right ventricular values.

Figure 11:
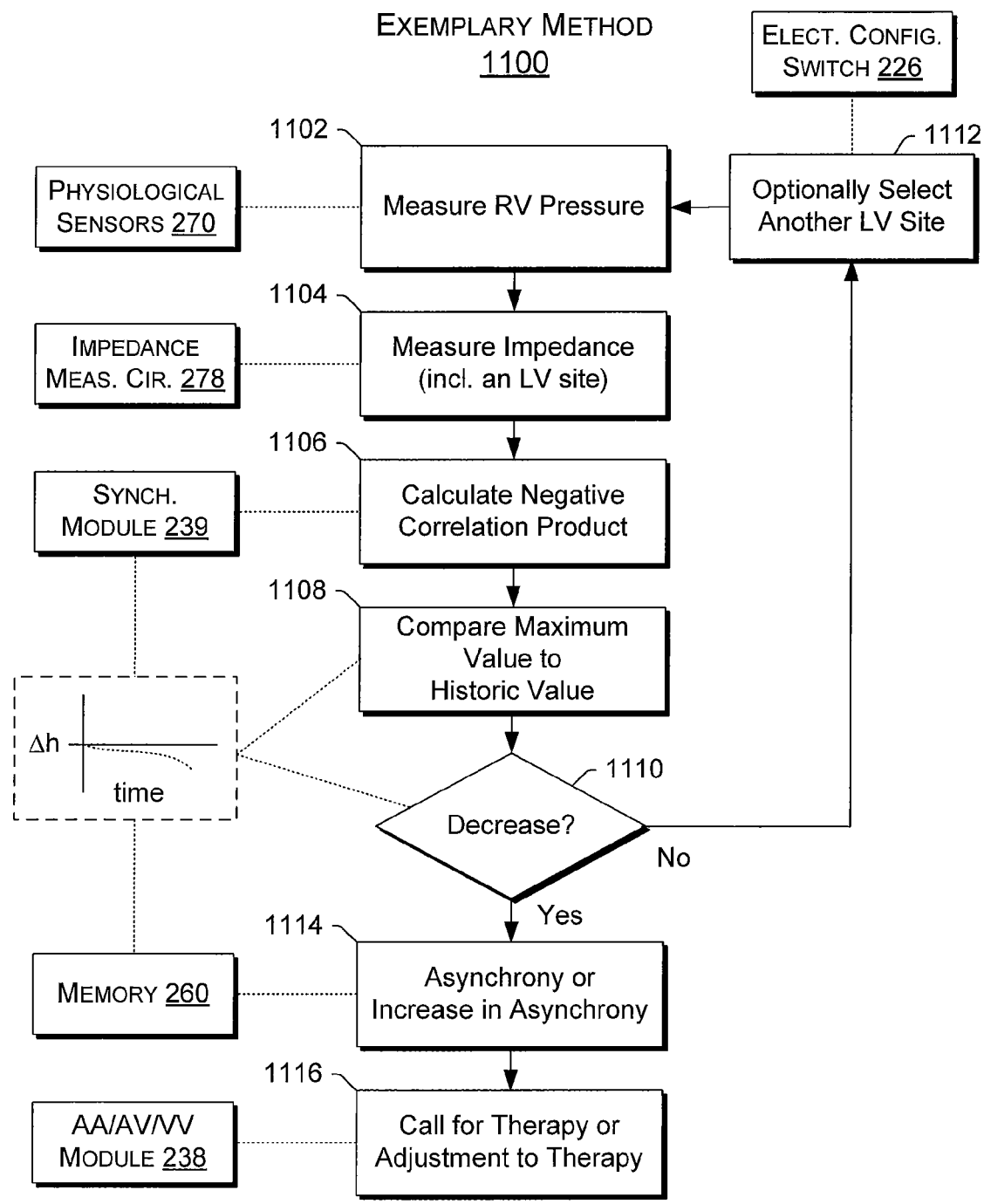
FIG. 11 is a block diagram of an exemplary method for deciding whether a change in ventricular synchrony has occurred.

FIG. 11 shows an exemplary method 1100 for deciding whether asynchrony exists or a change in synchrony/asynchrony has occurred. While various action blocks are shown in relationship to various modules of the exemplary implantable device 100 of FIG. 2, other hardware and/or software may be used to implement the method 1100. The method 1100 commences a measurement block 1102 that measures right ventricular pressure or a surrogate thereof. The measurement block 1102 may use one or more physiological sensors 270. For example, a lead based pressure transducer may be positioned in the right ventricle and connected to the device 100. Another measurement block 1104 measures impedance using at least one electrode associated with the left ventricle. The measurement block 1104 may use the impedance measurement circuit 278 of the device 100. For example, as appropriate, the microprocessor 220 may operate the electrical configuration switch 226 to select a particular electrode arrangement for measuring impedance as related to motion of the left ventricle. In general, the at least one electrode is positioned at a site other than the septal wall; noting that an electrode may be positioned at or proximate to the septal wall as the septal wall typically exhibits less motion than the left ventricular posterior wall or lateral wall.

According to the method 1100, a calculation block 1106 calculates a negative correlation product based at least in part on the measured right ventricular pressure and impedance. The calculation block 1106 may use the synchronization module 239 of the device 100 to calculate the negative correlation product or other indicator based at least in part on the measured right ventricular pressure and impedance. As already explained, right ventricular pressure and impedance measurements may be acquired over one or more respiratory cycles. Measured pressure and impedance values may be averaged or negative correlation products may be averaged.

A comparison block 1108 compares a maximum value of the negative correlation product for a particular cardiac cycle or an average of cardiac cycles to a historic value. For example, the height of a negative correlation product waveform may be used as a maximum value in such a comparison. A decision block 1108 decides if the maximum value of the negative correlation product has decreased. The comparison block 1108 and the decision block 1110 may use the synchronization module 239 of the device 100. For example, the synchronization module 239 may access historic information such as a past value, a series of past values, an average of past values, etc., which may then be used for a comparison and decision.

According to the method 1100, if the decision block 1110 decides that a decrease has not occurred, the method 1100 may continue at a selection block 1112 where another left ventricular site is selected for impedance measurement (e.g., per the measurement block 1104). For example, the exemplary arrangement 600 of FIG. 6 shows various electrodes for use in measuring impedance. The selection block 1112 may use the configuration switch 226 of the device 100, which may be controlled via a module (e.g., the synchronization module 239) of the microprocessor 220. To increase accuracy, the exemplary method 1100 may use more than one impedance path to acquire information related to left ventricular motion.

If the decision blocked 1110 decides that a decrease has occurred, the method 1100 enters a determination block 1114 that determines ventricular asynchrony exists or that an increase in the degree of ventricular asynchrony has occurred. The determination block 1114 may use the memory 260 of the device 100 to store information that indicates a change in synchrony has occurred. Such information may be used for any of a variety of purposes. An action block 1116 may follow that calls for an appropriate therapy or an adjustment to a therapy that aims to treat ventricular asynchrony. The action block 1116 may use the AA/AV/VV module 238 of the device 100, for example, to determine one or more pacing parameters.

The method 1100 may occur according to a schedule or in relationship to one or more events. For example, where an implantable device includes an algorithm to update or optimize one or more cardiac resynchronization therapy parameters, the algorithm may call for measurement of right ventricular pressure and left ventricular motion impedance to help assess degree of asynchrony. An exemplary method optionally uses right ventricular pressure and left ventricular motion impedance to select or adjust one or more cardiac resynchronization therapy parameters. For example, as a decrease in the height of a negative correlation product compared to a historic value reflects an increase in asynchrony, the height or decrease in height (e.g., percentage, etc.) may be used to adjust a pacing parameter such as interventricular delay (e.g., VV delay) for bi-ventricular pacing. As already mentioned, width of a negative correlation product for a particular cardiac cycle or an average over a number of cardiac cycles may be used as an indicator of asynchrony. Consequently, such a width may be used to adjust one or more pacing parameters.

As described herein, right ventricular pressure and left ventricular impedance may be measured and used as indicators of ventricular asynchrony or synchrony. In particular, a negative correlation product of right ventricular pressure and left ventricular impedance over a cardiac cycle or a portion of a cardiac cycle may be used to assess ventricular synchrony. Such measurements and correlation product calculations may occur in a manner that does not significantly burden resources of an implantable device. With respect to equipment, an exemplary implantable device may include a left ventricular electrode (e.g., surface vein, epicardial, etc.) and a right ventricular pressure sensor or a sensor to sense a surrogate for right ventricular pressure. As already mentioned, an accelerometer may be used to acquire information about left ventricular motion. Such accelerometer-based information may require some analysis to produce a waveform analogous to the aforementioned impedance waveforms. Consequently, use of impedance measurement circuitry, as used by many conventional implantable pacing devices, can provide an expeditious and relatively straightforward approach to assessing ventricular synchrony or asynchrony.

CONCLUSION

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

What is claimed is:

1. A method comprising: providing a maximum right ventricular systolic pressure value and corresponding time during a cardiac cycle; providing a left ventricular displacement value for the corresponding time; determining a product of the maximum right ventricular systolic pressure value and the magnitude of the left ventricular displacement value; and assessing ventricular synchrony for the cardiac cycle based at least in part on the product; and adjusting one or more cardiac pacing parameters based at least in part on the product.

2. The method of claim 1 wherein the providing a left ventricular displacement value comprises measuring impedance.

3. The method of claim 2 wherein the measuring impedance comprises use of a right ventricular lead and a left ventricular lead.

4. The method of claim 2 wherein the impedance decreases during contraction of the left ventricle.

5. The method of claim 1 wherein the assessing comprises comparing the product to a stored valued.

6. A method comprising: acquiring right ventricular pressure during a cardiac cycle; acquiring left ventricular impedance during the cardiac cycle; determining a product of the right ventricular pressure and the magnitude of the left ventricular impedance; and assessing ventricular synchrony for the cardiac cycle based at least in part on the product; and adjusting one or more cardiac pacing parameters based at least in part on the product.

7. The method of claim 6 wherein the acquiring left ventricular impedance comprises use of an electrode positioned on a lead inserted into the right ventricle and an electrode positioned on a lead inserted into a vein of the left ventricle.

8. The method of claim 6 wherein the acquiring left ventricular impedance comprises use of more than one electrode positioned on a lead inserted into a vein of the left ventricle.

9. The method of claim 6 wherein the acquiring left ventricular impedance comprises use of a first electrode to acquire a first impedance associated with a first impedance path and use of a second electrode to acquire a second impedance associated with a second impedance path.

10. The method of claim 6 wherein the assessing comprises comparing the product to a stored valued.

11. A method comprising: acquiring right ventricular pressure over at least one respiratory cycle; acquiring left ventricular impedance over at least one respiratory cycle; determining a product of the right ventricular pressure and the magnitude of the left ventricular impedance; and assessing ventricular synchrony for at least one cardiac cycle occurring during the at least one respiratory cycle based at least in part on the product; and adjusting one or more cardiac pacing parameters based at least in part on the product.

12. The method of claim 11 further comprising averaging the maximum right ventricular pressure values for each cardiac cycle that occurs during the at least one respiratory cycle and averaging the left ventricular impedance values that correspond to each of the maximum right ventricular values.

13. The method of claim 11 further comprising selecting the minimum peak right ventricular systolic pressure for use in the determining.

14. The method of claim 13 further comprising selecting the left ventricular impedance that corresponds to the minimum peak right ventricular pressure.

15. The method of claim 11 further comprising adjusting one or more cardiac pacing parameters based at least in part on the product.

16. A method comprising monitoring ventricular synchrony, the method: acquiring impedance during a cardiac cycle where the impedance decreases during contraction of the left ventricle; acquiring right ventricular pressure during a cardiac cycle; and assessing ventricular synchrony based at least in part on the correlation of the acquired impedance and the acquired right ventricular pressure; and adjusting one or more cardiac pacing parameters based at least in part on the correlation of the acquired impedance and the acquired right ventricular pressure.

* * * * *